(12) United States Patent
Bair, III et al.

(10) Patent No.: US 7,850,924 B2
(45) Date of Patent: Dec. 14, 2010

(54) USER NOTIFICATION OF TANK TYPE FOR TRIGAS ($CO_2/O_2/N_2$ SYSTEMS)

(75) Inventors: Richard H. Bair, III, Weaverville, NC (US); Bryan M. Elwood, Candler, NC (US)

(73) Assignee: Thermo Fisher Scientifiic Inc., Waltham, MA (US)

( * ) Notice: Subject to any disclaimer, the term of this patent is extended or adjusted under 35 U.S.C. 154(b) by 1324 days.

(21) Appl. No.: 10/152,021

(22) Filed: May 22, 2002

(65) Prior Publication Data

US 2003/0219907 A1   Nov. 27, 2003

(51) Int. Cl.
  *G01N 1/00* (2006.01)
(52) U.S. Cl. .................. 422/119; 422/98; 73/31.04
(58) Field of Classification Search ............... 436/181; 435/3; 73/861.27, 31.04, 1.06; 422/119, 422/82.13, 108, 110, 112, 105, 83, 84, 86, 422/94, 98, 99; 702/24, 104, 116
See application file for complete search history.

(56) References Cited

U.S. PATENT DOCUMENTS

| | | | | |
|---|---|---|---|---|
| 4,245,997 A | * | 1/1981 | Wiesner | 436/164 |
| 4,650,766 A | | 3/1987 | Harm et al. | 435/284 |
| 4,892,830 A | | 1/1990 | Findley et al. | 435/290 |
| 6,180,397 B1 | | 1/2001 | Binder | 435/303.1 |
| 6,265,210 B1 | | 7/2001 | Silley et al. | 435/303.1 |
| 6,632,674 B1 | * | 10/2003 | Warburton | 436/8 |
| 6,886,412 B2 | * | 5/2005 | Banno et al. | 73/861.27 |
| 6,987,448 B2 | * | 1/2006 | Catton et al. | 340/506 |

FOREIGN PATENT DOCUMENTS

JP    2001-041680    *    2/2001

* cited by examiner

*Primary Examiner*—Natalia Levkovich
(74) *Attorney, Agent, or Firm*—Wood, Herron & Evans, LLP

(57) ABSTRACT

An apparatus for notifying a user which gas tank(s) to connect to an enclosed chamber such as an incubator. The user inputs the desired setpoints for gasses such as $O_2$ and $CO_2$, and the corresponding gas level is determined. The determined gas level is compared with the setpoint of the gas and can display, which gas tank(s) should be hooked up to chamber.

22 Claims, 4 Drawing Sheets

USER NOTIFICATION OF TANK TYPE FOR TRIGAS ($CO_2/O_2/N_2$ SYSTEMS)

FIELD OF THE INVENTION

Embodiments of the present invention generally relate to an apparatus and method for use with a controlled gas atmosphere. More particularly, the apparatus and method of the present invention relates to notifying a user of the proper gas tank to be hooked up to a trigas incubator system.

BACKGROUND OF THE INVENTION

There are a number of commercial applications that utilizes a controlled gas atmosphere enclosure. For example, in the semiconductor industry, gases are injected into an enclosed chamber wherein one of the gases are plasmarized causing the gas to hit a target on a chamber lid causing the target's materials to deposit on a wafer. Other commercial applications include using controlled gasses to cultivate biological cultures in an enclosed chamber such as an incubator. It is desirable to maintain optimal conditions inside the incubator in order to promote the desired growth of the cultures. In a conventional incubator, gasses such as $O_2$, $N_2$, and $CO_2$ are introduced from their respective tanks into the chamber depending on the growing conditions desired. Typically, the user sets the $CO_2$ and $O_2$ setpoints and appropriate gas are added, if needed.

A conventional incubator is generally rectangular in shape and has up to five insulated walls (top, bottom, left side, right side, and rear). Each wall may have an inner space defined by the inner and outer surfaces of the insulated wall and the inner spaces are in communication with each other. An insulated front door together with the insulated walls complete the inner chamber of the incubator and the door is typically mounted on hinges on the front side of one of the side walls. The door allows access into the inner chamber where culture plates are placed or removed from a plethora of shelves provided therein.

Most biological incubators are either water jacket or forced draft. In the water jacket incubator, a water jacket is inserted in the inner space of the incubator. A heater is used to heat the water in the water jacket to the desired temperature. Because water can be heated evenly, the water jacket can evenly distribute the desired heat throughout the inner chamber. Such even heating is desired in order to provide a uniform temperature (for the biological cultures) throughout the chamber and to prevent "cold spots," which can cause condensation on the inner chamber walls.

Although heating of the chamber walls in the water jacket incubator is substantially uniform, the chamber atmosphere will stratify thermally if the chamber atmosphere is undisturbed. Due to the stratification, the temperature of the chamber is greater at the top of the chamber than at the bottom of the chamber. Consequently, if a constituent gas such as $CO_2$ is maintained in the chamber, the $CO_2$ will also stratify and the desired atmosphere for the cultures will not be maintained. Therefore, it is desirable to maintain a certain flow rate of constituent gases within the chamber to assure uniformity of the temperature and the constituent gas.

In order to circulate the air, a portion of the inner chamber is separated from the rest of the chamber by a wall to define a duct extending along the side of the chamber. The duct has an upper portion or the duct inlet, where a fan or a blower is used to circulate the air in the chamber and a lower portion (duct outlet) where air exits the chamber to be recirculated.

In the forced draft incubator, the inner space is lined with insulation instead of the water jacket. Heating of the chamber is provided by having a duct (previously described), a fan, and a heating element within the chamber. The air is typically circulated by the fan and heated by the heating element within the duct. The air is blown with more force than in the water jacket incubators in order to have more uniform circulation of the air and temperature in the chamber.

In most cases for proper culture growth, it is desirable to maintain a certain level of $CO_2$ and $O_2$ in the chamber. Thus, the $O_2$ enhancement levels or depletion changes dynamically depending on the $CO_2$ concentration. In order to maintain constituent gas levels such as $CO_2$ in conventional incubators, a probe can be inserted into the chamber to take a measurement of the gas level including $CO_2$, $O_2$. Based on the $CO_2$ setpoint selected by the user and the information from the probe, the user can determine if $O_2$ is needed or if $O_2$ needs to be purged by adding $N_2$ to the incubator. In a conventional trigas incubator, where the two main gases to be controlled are $CO_2$ and $O_2$, there can be a $CO_2$ tank connected to an inlet and $O_2$ and $N_2$ connected to another inlet. A manual switch can switch between the $O_2$ and $N_2$ tanks depending on the level of $O_2$ desired in the incubator.

If the user, based on the information from the probe and the $CO_2$ setpoint determines that $O_2$ is needed by mistake, when $N_2$ is really needed, the user can hook up the wrong tank. With the wrong tank in place, the wrong gas will be injected, thereby causing the results from the cultures to be inaccurate or possibly destroying weeks, or months worth of research. Additionally, if too much $O_2$ is added, then an explosive situation can be created in the chamber.

Therefore, there is a need for a notification system to allow a user to know which tanks to attach to the incubator for a given setpoint of a gas for improved culture growth. Additionally, there is a need for a notification system that helps to prevent the user from hooking up the wrong tank.

SUMMARY OF THE INVENTION

The present invention generally relates to a notification system that when a setpoint for a gas is inputted, a notification is provided to the user indicating an appropriate gas source to connect to an incubator. The notification system helps to ensure that the appropriate gases are available for proper growth of the cultures.

One embodiment of the present invention include a notification apparatus for an enclosed chamber that includes a setpoint setter that sets a setpoint threshold concentration for a first gas and a second gas, a gas concentration evaluator that determines the concentration of second gas based on the first gas, a gas concentration comparator that determines if the determined concentration of the second gas meets the setpoint threshold of the second gas, and an indicator that indicates if the determined concentration of the second gas meets the setpoint threshold of the second gas, wherein the setter, evaluator, comparator and indicator are in communication with each other. A user can set the setpoint using the setpoint setter. The first gas and the second gas can be selected from a group that includes $CO_2$, $O_2$, and $N_2$. The evaluator can determine the concentration of the second gas using an algorithm that includes a formula $y=-0.297x+20.85$ and/or $y=-0.209x+20.9$, where y can be $O_2$ % concentration and x can be $CO_2$ % setpoint. The gas concentration comparator can determine if the determined concentration of the second gas is higher or lower than the setpoint threshold of the second gas. The indicator can indicate visually and/or audibly and can notify a user what gas tank needs to be connected to the incubator.

A method of notifying a user of tank type can include setting setpoints of a first gas and a second gas, calculating the level of the second gas based on the setpoint of the first gas, comparing the calculated level of the second gas level to the setpoint of the second gas, and displaying the result to the user. Calculating the setpoint can be done by using an algorithm that can include a formula $y=-0.297x+20.85$ and/or $y=-0.209x +20.9$, where y can be $O_2$ % concentration and x can be $CO_2$ % concentration. Displaying the result can include informing the user what gas tank needs to be connected to the incubator. The first and second gas can be selected from $CO_2$, $O_2$, and $N_2$.

A notification system for an enclosed chamber that includes a means for setting setpoints for a first gas and a second gas, a means for evaluating the level of the second gas, a means for comparing the evaluated level of second gas to the setpoint of the second gas, and a means for indicating the result to the user. The means for setting can be a user interface. The first gas and the second gas may be selected from $CO_2$, $O_2$, and $N_2$. The means for comparing can compare if the evaluated concentration of the second gas is higher or lower than the setpoint threshold of the second gas. The means for indicating can include notifying the user what gas tank needs to be connected to the chamber.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The present invention notifies a user of the proper tank(s) of gas that should be hooked up to an incubator at given setpoints for gasses such as $CO_2$ and $O_2$. The term "hooked up" as used herein can mean that the user is required to attach the correct tank(s) of gas or the user can confirm that the required tank(s) are already attached for use. An embedded or remotely located notification apparatus can be used to calculate the proper level of $O_2$ required using setpoints for $CO_2$ and $O_2$ and indicates whether the $O_2$ or the $N_2$ tank is required to be hooked up. "Notify" as used herein can be a visual, audible or other means so long as the user knows which tank(s) to hook up at particular setpoints. Notify a user can occur at the incubator itself, for example via an integrated display or remotely such as another display, fax, email, phone, computer or any means that will allow the user to know which tank(s) to hook up.

Figure 1:
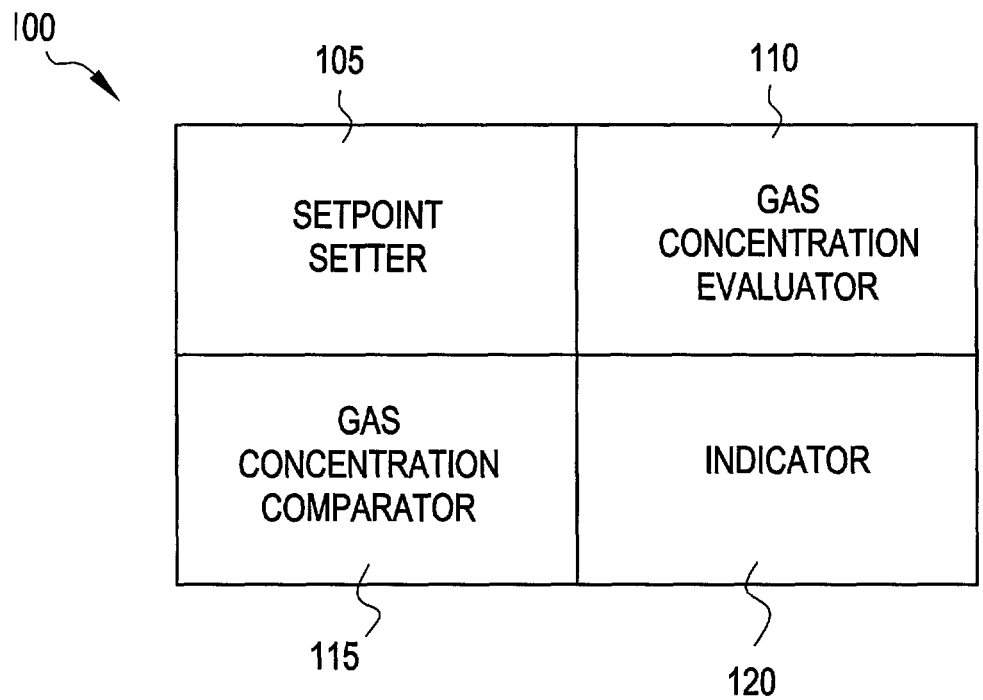
FIG. 1 is a notification apparatus of the present invention.

FIG. 1 is a notification apparatus 100 of the present invention. The notification apparatus 100 can include a setpoint setter 105, a gas concentration evaluator 110, a gas concentration comparator 115, and an indicator 120. The notification apparatus 100 can be embedded in an incubator or located remotely such as in a computer. The setter 105 can be an interface that can be in the form of a data entry keypad. The setter 105 may be integrated with the incubator or located remotely at a user station, such as a computer. The setter 105 can be used to set the setpoints or the concentrations of the desired gases such as $CO_2$ and $O_2$ that will be run in the incubator. The notification apparatus 100 can also include a gas concentration evaluator 110. The evaluator 110 can evaluate or calculate the corresponding level of $O_2$ that will be in the incubator based on the $CO_2$ setpoint. The evaluator 110 can also execute an algorithm 310, 320, such as the algorithms illustrated in FIG. 3 (below). The algorithm 310, 320 may be any algorithm that calculates the corresponding $O_2$ level based on the $CO_2$ setpoint and/or $O_2$ setpoint and/or any other desired gas. The gas concentration comparator 115 can compare the $O_2$ level calculated by the evaluator 110 to the $O_2$ setpoint previously set. The comparator 115 compares to see if the $O_2$ level is higher or lower than the $O_2$ setpoint and displays the result to an indicator 120. The indicator 120 can notify the user audibly or visually which tank(s) to hook up. A previously determined sound (pitch, type, etc.) could be associated with a particular tank of gas. The indicator 120 can also notify the user via a display that is integrated with the incubator or remotely located such as a computer.

Figure 2:
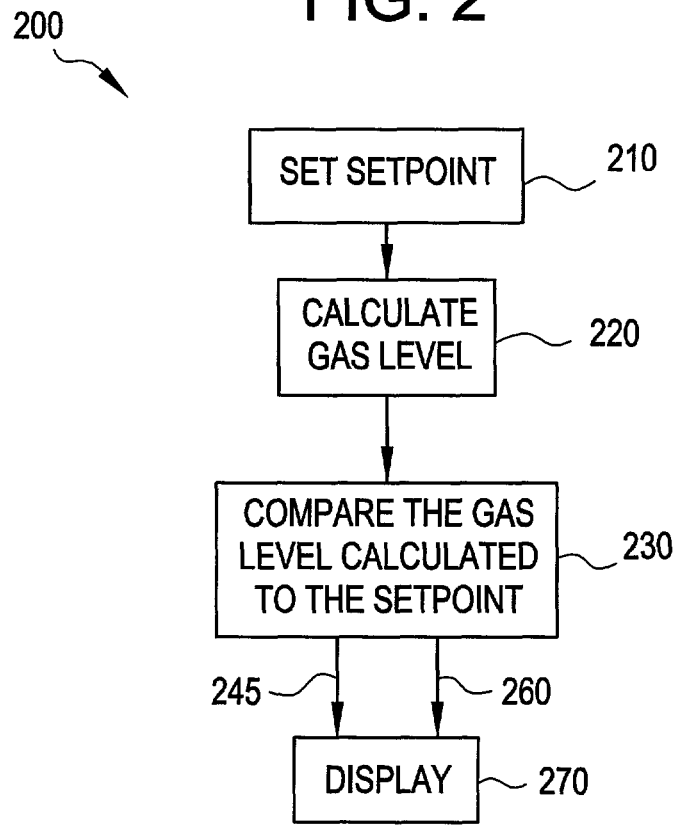
FIG. 2 is a flowchart of an embodiment of the present invention.
Figure 3:
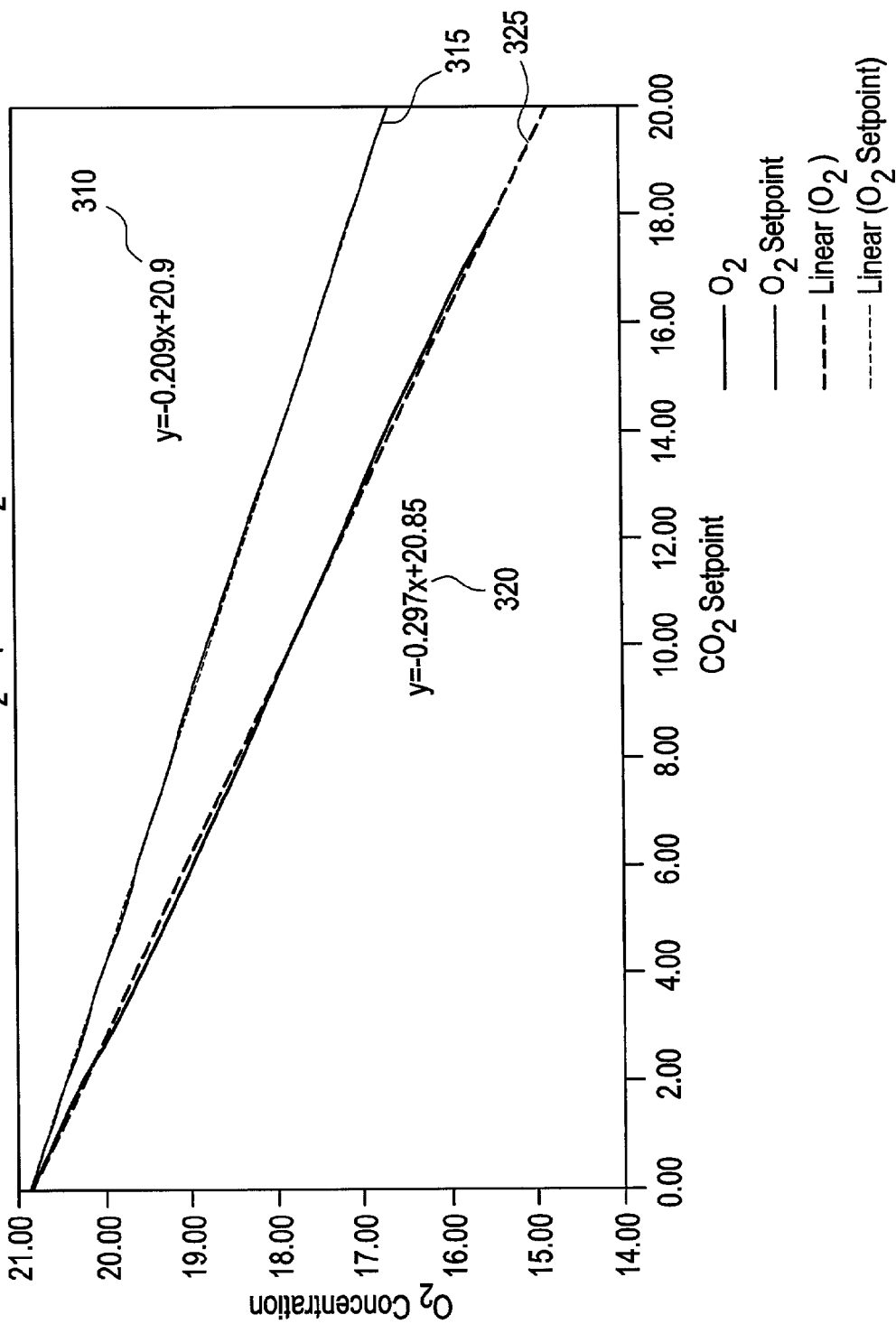
FIG. 3 is a graph of an algorithm of the present invention.
Figure 4:
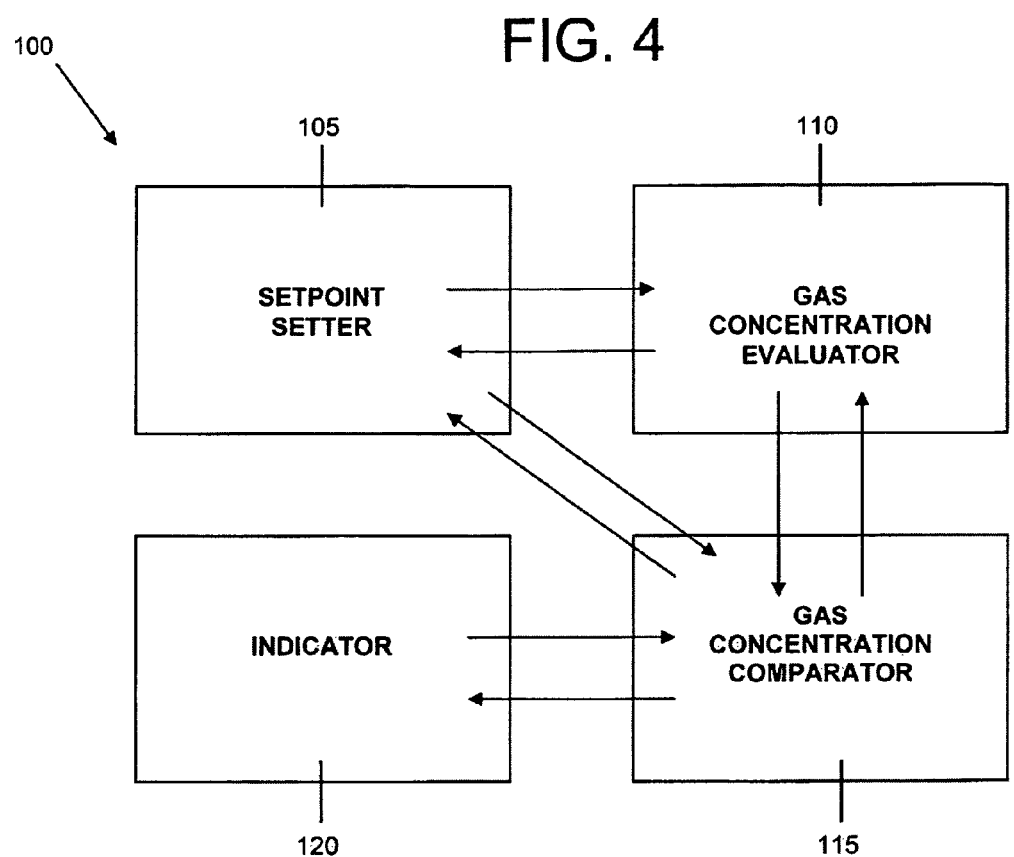
FIG. 4 illustrates a notification apparatus in accordance with an embodiment of the present invention.
Figure 5:
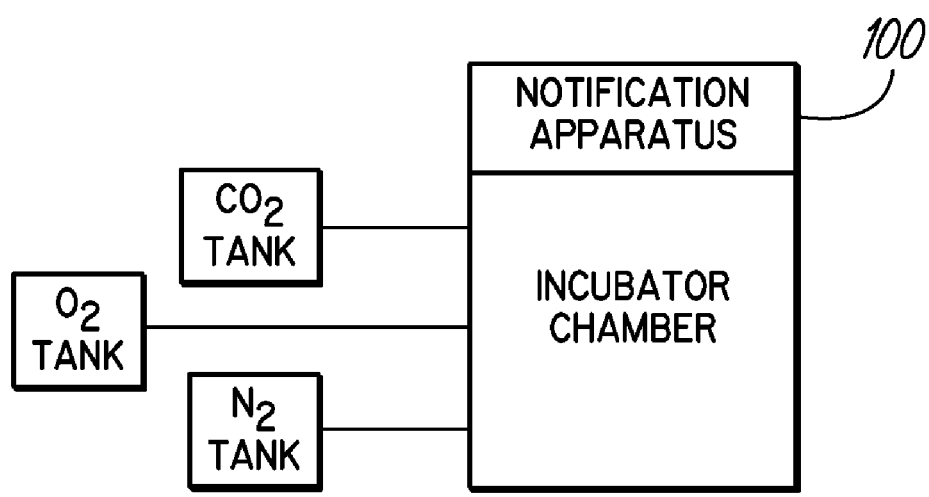
FIG. 5 is a diagrammatic view of an incubator incorporating the notification apparatus of FIG. 1 according to one embodiment of the present invention.

FIG. 2 is a flowchart of an embodiment of the present invention, and FIG. 4 illustrates a notification apparatus in accordance with an embodiment of the present invention. The notification method 200 may begin with step 210 where the setpoints for the desired gasses, typically $CO_2$ and/or $O_2$, can be set with the setter 105. The setpoints can be relayed to the evaluator 110. At step 220, the evaluator 110 can calculate the corresponding $O_2$ level required for the $CO_2$ setpoint using the algorithm 310, 320 (FIG. 3). At step 230, the comparator 115 compares the $O_2$ gas level calculated by the evaluator 110 with the $O_2$ setpoint. If the $O_2$ setpoint is lower than the $O_2$ level calculated by the comparator 115, then $N_2$ is required to be injected from the incubator to purge the $O_2$ from the incubator in order to reach the $O_2$ setpoint. If the $O_2$ setpoint is higher than the $O_2$ level calculated by the comparator 115, then $O_2$ is required to be injected into the incubator to enhance the current $O_2$ in order to reach the $O_2$ setpoint.

Still referring to FIG. 2, if $N_2$ is required, a signal 245 can be sent to the display at step 270 notifying the user that at least one $N_2$ tank is required to be hooked up to the incubator. If $O_2$ is required, a signal 260 can be relayed to the display at step 270 notifying the user that at least one $O_2$ tank is required to be hooked up to the incubator. Depending on the information on the display, the user can add the appropriate tank(s), can move a switch to allow access to the proper tank or can confirm that the correct tank(s) are connected. Additionally, at the same time the user can also view the tank's volume indicator to see if there is enough of the appropriate gas available in the tank or if the tank needs to be replaced.

FIG. 3 is a graph 300 of an algorithm of the present invention. In a preferred embodiment, the graph 300 can have an X and a Y axis, wherein the X axis may be the $CO_2$ setpoint or $CO_2$ % concentration and the Y axis may be the $O_2$ % concentration. A first line graph 325 can be generated using the formula y=−0.297x +20.85, (which is numbered 320 in FIG. 3), wherein y is the $O_2$ % concentration and x is the $CO_2$ setpoint. Thus, if the user wants an $O_2$ setpoint of 19% (not inputted into algorithm) and a $CO_2$ setpoint of 10%, the $O_2$ % concentration (according to the algorithm) or y is 17.88%. The $O_2$ % concentration in the incubator at that $CO_2$ setpoint should be around 17.88% as determined by step 240. Therefore, at $O_2$ setpoint of 19%, $O_2$ will be needed to bring the $O_2$ level from 17.88% to 19% in the incubator. The display at step 270 can notify the user that $O_2$ is required. The user can determine if the $O_2$ tank is hooked up or if it needs to be hooked up. Additionally, at this time, the user can also check to see if there is enough $O_2$ in the tank or if a new tank is needed. If the $O_2$ level is satisfactory as determined at step 240, the display can show the satisfactory conditions, and that no action may be required by the user.

Still referring to FIG. 3, a second line graph 315 of a second embodiment of the algorithm is also illustrated. Again the graph can have an X and a Y axis, wherein the X axis may be the $CO_2$ setpoint or $CO_2$ % concentration and the Y axis may be the $O_2$ % concentration. The second line graph 315 may be generated using the formula y=−0.209x+20.9, (which is numbered 310 in FIG. 3) wherein y may be the $O_2$ % concentration and x may be the $CO_2$ setpoint. Thus, if a user wants an $O_2$ setpoint of 17% (not inputted into the algorithm), and a $CO_2$ setpoint of 10%, the $O_2$% concentration (according to the algorithm) or y is 18.81%. The $O_2$ % concentration in the incubator at that $CO_2$ setpoint should be around 18.81% as determined by step 240. Therefore, at an $O_2$ setpoint at 17%, $N_2$ is required to be injected into the incubator to purge the $O_2$ level from 18.81% to 17%. The display at step 270 can notify the user that $N_2$ is required to be hooked up to the incubator. The user will then determine if the $N_2$ tank is hooked up or if it needs to be hooked up. Additionally, at this time, the user can also check to see if there is enough $N_2$ in the tank or if a new tank is needed.

The algorithm used in step 220 can be the algorithm 310 or 320 depending on the preference of the user. Although the gases described herein are mainly $CO_2$, $O_2$, and $N_2$, the notification system disclosed can be utilized with any combination of gases that are used in a chamber such as an incubator. Additionally, the invention disclosed herein may also be used with other gas systems.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A notification apparatus for an enclosed chamber, comprising:

a setpoint setter that sets a setpoint threshold concentration for a first gas and a second gas, the first gas and the second gas being different gases;

a gas concentration evaluator that executes an algorithm that calculates a concentration for the second gas based on the setpoint threshold concentration of the first gas;

a gas concentration comparator that calculates if the concentration of the second gas calculated by the evaluator meets the setpoint threshold concentration of the second gas; and an indicator that indicates whether the determined concentration of the second gas for the enclosed chamber as calculated by the evaluator and the comparator meets the setpoint threshold concentration of the second gas, wherein the setter, evaluator, comparator and indicator are in communication with each other.

2. The notification apparatus of claim 1, wherein a user sets the setpoint threshold concentration for the first gas and second gas using an interface of the setpoint setter.

3. The notification apparatus of claim 1, further comprising the first gas, wherein the first gas is selected from a group consisting of $CO_2$, $O_2$, and $N_2$.

4. The notification apparatus of claim 1, further comprising the second gas, wherein the second gas is selected from a group consisting of $CO_2$, $O_2$, and $N_2$.

5. The notification apparatus of claim 1, wherein the evaluator calculates the concentration of the second gas using an algorithm that comprises a formula y=−0.297x +20.85.

6. The notification apparatus of claim 5, wherein y is $O_2$% concentration and x is $CO_2$% setpoint.

7. The notification apparatus of claim 1, wherein the evaluator determines the concentration of the second gas using an algorithm that comprises a formula y=−0.209x+20.9.

8. The notification apparatus of claim 7, wherein y is $O_2$% concentration and x is $CO_2$% setpoint.

9. The notification apparatus of claim 1, wherein the gas concentration comparator determines if the determined concentration of the second gas is higher, lower, or equal to the setpoint threshold of the second gas.

10. The notification apparatus of claim 1, wherein the indicator is a visual indicator.

11. The notification apparatus of claim 1, wherein the indicator is an audible indicator.

12. The notification apparatus of claim 1, wherein the indicator notifies a user that a gas tank needs to be connected to the chamber.

13. A notification system for an enclosed chamber comprising:

means for setting setpoints for a concentration of a first gas and a concentration of a second gas, the first gas and the second gas being different gases;

means for evaluating the concentration of the second gas with respect to the concentration of the first gas using an algorithm based on setpoints set for the first and second gas communicated to the means for evaluating the concentration of the second gas from the means for setting setpoints;

means for comparing the evaluated concentration of the second gas to the setpoint concentration of the second gas based on the concentration determined by the means for evaluating and communicated to the means for comparing; and means for indicating the concentration of the second gas to the user as determined by the means for comparing and communicated from the means for comparing to the means for indicating.

14. The notification system of claim 13, wherein the means for setting is a user interface.

15. The notification system of claim 13, further comprising the first gas, wherein the first gas is selected from a group consisting of $CO_2$, $O_2$, and $N_2$.

16. The notification system of claim 14, further comprising the second gas, wherein the second gas is selected from a group consisting of $CO_2$, $O_2$, and $N_2$.

17. The notification system of claim 13, wherein the means for comparing compares if the evaluated concentration of the second gas is higher lower or equal to than the setpoint threshold of the second gas.

18. The notification system of claim 13, wherein the means for indicating notifies the user that a gas tank needs to be connected to the chamber.

19. The notification apparatus of claim 1, wherein the setpoint setter comprises a data entry keypad.

20. The notification apparatus of claim 11, wherein the audible indicator provides a predetermined sound for a particular tank of gas.

21. The notification apparatus of claim 1, wherein information from the setpoint setter related to the setpoint threshold concentration of the first gas is communicated to the evaluator and information related to the setpoint threshold concentration of the second gas is communicated to the comparator.

22. The notification apparatus of claim 1, wherein information from the comparator is communicated to the indicator, such that the indicator indicates when the determined concentration of the second gas meets the setpoint threshold concentration of the second gas.

\* \* \* \* \*

UNITED STATES PATENT AND TRADEMARK OFFICE
CERTIFICATE OF CORRECTION

PATENT NO. : 7,850,924 B2  
APPLICATION NO. : 10/152021  
DATED : December 14, 2010  
INVENTOR(S) : Bair, III et al.

Page 1 of 1

It is certified that error appears in the above-identified patent and that said Letters Patent is hereby corrected as shown below:

On the Title Page, Item (57) Abstract, change "and can display, which gas tank(s)" to --and can display which gas tank(s)--.

In column 1, lines 14-15, change "applications that utilizes a controlled gas" to --applications that utilize a controlled gas--.

In column 1, line 17, change "wherein one of the gases are plasmarized" to --wherein one of the gases is plasmarized--.

In column 1, line 27, change "appropriate gas are added, if needed." to --appropriate gas is added, if needed.--.

In column 3, line 13, change "an enclosed chamber that includes a means" to --an enclosed chamber includes a means--.

In column 5, line 58, change "spirits and scope of the invention." to --spirit and scope of the invention.--.

In claim 17, column 7, line 11, change "is higher lower or equal to than the setpoint" to --is higher, lower, or equal to the setpoint--.

Signed and Sealed this  
Thirty-first Day of May, 2011

David J. Kappos  
*Director of the United States Patent and Trademark Office*